(12) United States Patent
Geha et al.

(10) Patent No.: US 10,031,116 B2
(45) Date of Patent: Jul. 24, 2018

(54) MULTIVARIATE GENETIC EVALUATION OF MAIZE FOR GRAIN YIELD AND MOISTURE CONTENT

(71) Applicant: Agrigenetics, Inc., Indianapolis, IN (US)

(72) Inventors: Makram Geha, Indianapolis, IN (US); Kelly R. Robbins, Indianapolis, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 738 days.

(21) Appl. No.: 13/905,618

(22) Filed: May 30, 2013

(65) Prior Publication Data

US 2013/0325355 A1 Dec. 5, 2013

Related U.S. Application Data

(60) Provisional application No. 61/653,295, filed on May 30, 2012.

(51) Int. Cl.
| | |
|---|---|
| *G06F 17/16* | (2006.01) |
| *G01N 33/00* | (2006.01) |
| *G06F 19/18* | (2011.01) |
| *G06F 19/24* | (2011.01) |

(52) U.S. Cl.
CPC ......... *G01N 33/0098* (2013.01); *G06F 17/16* (2013.01); *G06F 19/18* (2013.01); *G06F 19/24* (2013.01)

(58) Field of Classification Search
None
See application file for complete search history.

(56) References Cited

PUBLICATIONS

Crossa, "Prediction of genetic values of quantitative traits in plant breeding using pedigree and molecular markers," Genetics, vol. 186.2, p. 713-724, 2010.*

Datta, "Genetic divergence among maize (*Zea mays* L.) inbreds and restricting traits for group constellation," Indian J, vol. 64, p. 201-207, 2004.*

Wisser, R. et al., "Multivariate analysis of maize disease resistance suggests a pleiotropic genetic basis and implicates a GST gene," PNAS, 2011, 108, 7339-7344.

Misztal, I. et al., "Implementation of Single- and Multiple-Trait Animal Models for Genetic Evaluation of Holstein Type Traits," J. Dairy Science, 1993, 76, 1421-1432.

Henderson, C.R., "Best Linear Unbiased Estimation and Prediction under a Selection Model," Biometrics, 1975. 31, 423-447. (Summary only).

Yu, J. et al., "A unified mixed-model method for association mapping that accounts for multiple levels of relatedness," Nature Genetics, 2006, 38, 203-208.

Henderson, C.R., "Selection index and expected genetic advance," Statistical Genetics and Plant Breeding, 163, 141-163, 1963.

Lund, M.S. et al., "Multitrait Fine Mapping of Quantitative Trait Loci Using Combined Linkage Disequilibria and Linkage Analysis," Genetics, 2003, 163, 405-410.

Gilmour, A.R. et al., ASReml User Guide, 2009, Software Version 3.0.

Henderson, C.R., "Selection index and expected genetic advance," Statistical Genetics and Plant Breeding, 1963, 982: 141-163.

* cited by examiner

*Primary Examiner* — G. Steven Vanni

(74) *Attorney, Agent, or Firm* — Marcos P. Rivas; Barnes & Thornburg LLP

(57) ABSTRACT

A method for genetic evaluation of an inbred plant includes construction of a phenotypic trait database incorporating at least two numerically representable phenotypic traits in a first plant population. Methods for selecting an inbred plant or hybrid plant based on genetic values can be obtained using a multivariate mixed model analysis of such a relationship matrix comprising at least two numerically representable phenotypic traits.

16 Claims, No Drawings

MULTIVARIATE GENETIC EVALUATION OF MAIZE FOR GRAIN YIELD AND MOISTURE CONTENT

CROSS-REFERENCE TO RELATED APPLICATIONS

This application claims priority to U.S. Provisional Patent Application No. 61/653,295, filed May 30, 2012, the disclosure of which is hereby incorporated by reference in its entirety.

FIELD OF THE DISCLOSURE

The present disclosure relates to the genetic/phenotypic evaluation of maize. In some embodiments, methods are provided for evaluating an inbred maize line, for example, to improve a maize breeding program.

BACKGROUND

The polygenic model has been used in attempts to enhance selection efficacy in plant breeding programs. By observation and careful measurements of results of various parental-offspring distributions, both in plants and animals, and by expressing the genetic relationships in mathematical correlations, a complex mathematical theory emerged. See, e.g., Wright (1977) *Evolution and the Genetics of Populations*, vol. 5, University of Chicago Press, Chicago, Ill.

A basic tenant of this theory is the expression of phenotypic distribution in terms of its variance and dissection of that variance into its causative components. By studying the variance in offspring distributions where the offspring result from various types of crosses, and by determining the correlation between phenotypic distributions of different pedigree relationships (parent-offspring, offspring of the same cross, subsequent generations, e.g., $F_2$-$F_3$,) it was determined that the phenotypic variance ($V_P$) had as basic components genotypic variance ($V_G$) and environmental variance ($V_E$). In a simple case, the variance of plants of the same genotype grown in different environments provides an estimate of the effects of environment. Factors contributing to the environmental variance include year of growth and differences in the soil composition of plots of land.

In turn, each of these components could be further subdivided, for example, by separating $V_G$ into additive ($V_A$), dominance ($V_D$) and epistatic ($V_I$) components. The components of the variance could be estimated by breeding experiments. These values were then used to predict results of other breeding crosses. Response to selection was found to be a function of the heritability of the trait, the selection differential and the intensity of selection.

The heritability ($h^2$) of a trait is broadly defined as $$h^2 = V_G/V_P, \text{or more narrowly,} \quad (1)$$

$$h^2 = V_A/V_P \quad (2)$$

and is a predictor of the degree to which values of traits may be transmitted from parents to offspring.

Advancement of hybrid and inbred lines are conducted based on large scale trials and through several statistical analysis methodologies. Lines are advanced for meeting specific criteria for grain yield, moisture content as well as certain key agronomics. The genetic evaluation of the different lines provides an estimate of the general combining abilities (GCA) of inbred lines (in other words, an evaluation of their value as parents of hybrids) as well as an estimate of the specific combining ability (SCA), reflecting the evaluation of the hybrid itself.

The goal of plant breeding in corn is to develop inbred parent lines that contribute various desirable traits to the hybrids in which they are used. These traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, stalk strength, root strength, ear retention, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations, the heterozygous condition gives way to homogeneous lines as a result of self-pollination and selection. Typically in the pedigree method of breeding, five or more generations of selfing and selection is practiced: F1; F2; F3; F4; F5, etc. These selfing generations are sometimes designated as S0, S1, S2, etc with S0 being an equivalent to F1 while S2 is an equivalent to F3, etc.

Backcrossing can be used to improve an inbred line or to develop a closely related new inbred line depending on the number of backcross generations and backcross methods employed. Backcrossing transfers a specific desirable trait from one inbred or source to an inbred that lacks that trait. This can be accomplished, for example, by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the nonrecurrent parent. After five or more backcross generations with selection for the desired trait, the progeny will be heterozygous for loci controlling the characteristic being transferred, but will be like the superior parent for most or almost all other genes. After the last backcross generation, the inbred line would be selfed to give pure breeding progeny for the gene(s) being transferred.

A single cross hybrid corn variety is the cross of two inbred parent lines, each of which has a genotype which complements the genotype of the other. The hybrid progeny of the first generation is designated F1. In the development of hybrids, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny (F1). During the inbreeding process in corn, the vigor of the lines decreases. Vigor is restored when two unrelated inbred lines are crossed to produce the hybrid progeny (F1). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)× (C×D). Much of the hybrid vigor exhibited by F1 hybrids is lost in the next generation (F2). Consequently, seed from hybrid varieties is not used for planting stock.

Corn is an important and valuable field crop. Thus, a continuing goal of plant breeders is to develop consistent performing, high-yielding corn hybrids that are agronomically sound based on stable inbred lines. The reasons for this goal are obvious: to maximize the amount of grain produced with the inputs used and minimize susceptibility of the crop to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few, if any, individuals having the desired genotype may be found in a large F2 or S1 population. Typically, however, the genotype of neither the parents nor the desired genotype is known in any detail. An agronomically acceptable F1 hybrid will come from a cross between two superior inbred parental lines. There is no assurance that either of these parental lines will produce a superior hybrid when crossed with a different inbred parent line. Thus, the selection or combination of the two parental inbreds provides a unique hybrid that demonstrates characteristics and performance levels that differ from that obtained when either of the parents is crossed with a different inbred parent line.

Once the superior combination of two parental lines is determined by the testing and selection of the F1 hybrid, that F1 hybrid and the performance traits and characteristics of the hybrid can be indefinitely reproduced so long as the parental inbreds are maintained in their homozygosity and the quality and production procedures are accomplished to the purity standards determined by the seed industry regulation.

This evaluation has been so far performed separately for grain yield and moisture through use of a univariate mixed model analysis approach. The results are presented as a predicted value, generally referred to as a Best Linear Unbiased Prediction (BLUP). Along with the BLUP values, the accuracy of prediction can be calculated for each of the BLUP values. Accuracy is a measure that indicates how well the predicted values correlate with the "true" genetic values and can take on any value between 0 and 1. The closer the accuracy is to 1, the closer the predicted genetic value is to the true genetic value.

It is noteworthy that phenotypic measurements of inbred maize lines are rarely used for genetic evaluations in the seed industry; rather, records of hybrid (offspring) lines are normally used to draw inferences about the parent lines.

Wisser et al. (2011), Proc. Natl. Acad. Sci. USA 108(18): 7339-44, used data recorded directly on inbred lines to study the genetics of multiple disease resistance in inbred maize lines. The objective of the study was to draw inferences on multiple disease resistance traits through variance component estimation and to test the hypothesis that markers are associated with multiple disease resistance traits. Wisser's method was based on a multi-variate mixed model; however his model differs in several aspects from the model disclosed herein. First, Wisser's inbred lines were not separated into male and female lines. Second, the relationship matrix used was constructed for all the lines in the study. Third, Wisser incorporated a subpopulation effect in his model as a fixed effect. Fourth, because the analysis was based on inbred data, specific combining ability (SCA), which must be derived from hybrid offspring produced from a specific male and female parental cross, could not be calculated.

In summary, although the two approaches are based on a multivariate mixed model approach, they differ in the components, the type of data to be analyzed and the final application of the results.

BRIEF SUMMARY OF THE DISCLOSURE

Described herein is a multivariate mixed model analysis approach that provides higher accuracy of prediction of the genetic evaluation of maize inbred and hybrid lines for grain yield and moisture content compared to the art-recognized univariate mixed model analysis approach.

Some embodiments disclose a method for genetic evaluation of an inbred plant involving construction of a phenotypic trait database incorporating at least two numerically representable phenotypic traits in a first plant population. In particular embodiments, a relationship matrix is constructed using the phenotypic trait database, and then applied in a multivariate mixed model analysis to obtain a genetic value for the plant. In examples, the at least two numerically representable phenotypic traits may be correlated traits, for example and without limitation, grain yield and moisture content.

Also described herein are methods for selecting an inbred plant or hybrid plant based on genetic values obtained using a multivariate mixed model analysis of such a relationship matrix comprising at least two numerically representable phenotypic traits.

The foregoing and other features will become more apparent from the following detailed description of several embodiments.

DETAILED DESCRIPTION

I. Overview of Several Embodiments

Genetic evaluation of a given trait may be described using Best Linear Unbiased Prediction (BLUP). The accuracy of BLUP depends on several factors such as the number of relatives that exists within the population being evaluated, the number of observations made for an individual and/or its relatives, and the variance components of the population. Generally, the more observations that are made for an individual and/or its relatives, the better will be the prediction of its genetic value, and therefore the higher the accuracy of that prediction.

In the genetic evaluation of livestock, attributes known to be correlated are seldom analyzed individually. In these instances, a multivariate mixed model approach is used, with the different attributes analyzed simultaneously. In livestock, this approach has been shown to provide increases in the accuracy of prediction compared to the univariate approach. Misztal et al. (1993), J. Dairy Sci. 76(5).

In maize evaluation, this approach has not been extensively utilized, especially when evaluating lines for grain yield and moisture content. In fact, a search of the literature failed to yield any reference on such an approach being utilized in the genetic evaluation of maize Grain yield and moisture content are, in fact, correlated attributes. In maize, the multi-variate analysis approach has been mostly limited to non-genetic evaluation studies (e.g. Lee et al., 2005; Williams et al., 2009 . . . ), although several correlations are known to exist among the common attributes used for evaluating maize (e.g. yield and moisture content, . . . ).

A multivariate mixed model approach was developed by the Quantitative Genetics group at Dow AgroSciences for genetic evaluation of maize inbred lines. The disclosed model is an extension of the univariate model presented by Bernardo (1992), which has been the traditional method applied at DAS for conducting maize genetic evaluation. The main objective of the disclosed multivariate mixed model approach is to provide genetic values of inbred lines to be used for creating new breeding populations. In addition, variance component estimates resulting from the analysis can be used to evaluate the efficiency of the genetic selection program adopted at DAS.

The disclosed multivariate mixed model approach was evaluated against the art-recognized univariate analysis. The two approaches were evaluated based on differences in accuracy. The data was obtained from several commercial lines as well as several lines currently in the variety development pipeline. Overall, seven different data sets were used as pilot data for the comparison. For GCA, increases in accuracy using the multivariate approach averaged between 1% and 45%, depending on the data set. For SCA, increases in accuracy from using the multivariate approach averaged between 0.3% and 7%, depending on the data set. The multivariate mixed model analysis approach provides higher accuracy of prediction of the genetic evaluation of maize hybrid and inbred lines for grain yield and moisture content compared to the currently adopted univariate mixed model analysis approach.

The multivariate mixed model approach has the potential to be used in other crops, or to be extended to incorporate other attributes of interest within a single crop (i.e. not limited to only yield and moisture content).

The new model allows genetic evaluation of multiple traits of interest to be conducted simultaneously, compared to the previous method, which required the evaluation to be conducted on a per-trait basis. Inbred lines are defined as either male or female lines and a relationship matrix for each parent line is constructed and fitted in the mixed model for the male and female GCA based on pedigree and marker information. A dominance relationship matrix may also be constructed to allow fitting the SCA effect. The new model uses field trial data of hybrid progeny to evaluate the genetic value of inbred lines, and provides improved accuracy of prediction of genetic values (GCA and SCA). Once the analysis is conducted, the results are provided for each parent line as genetic values for each trait of interest.

II. Abbreviations

BLUP best linear unbiased prediction
GCA general combining ability
SCA specific combining ability III. Terms Accuracy: As used herein, the term, "accuracy" may generally refer to the correlation between the predicted genetic value (e.g., the BLUP value) and the "true" genetic value, and generally assume a value between 0 and 1. The closer the accuracy is to 1, the close the predicted value is to the true genetic value. In particular embodiments, accuracy in a plant line is determined based on the prediction error variance (PEV) (i.e. the variance of genetic value).

Agronomic trait: As used herein, the term "agronomic trait" may refer to traits such as, for example and without limitation, increased or altered growth characteristics, stress tolerance (e.g., drought, NUE, heat, salt, etc.), disease and insect resistance, modified seed oil composition, modified seed protein, and expression of one or more transgene(s) in a transgenic organism. Some examples include agronomic traits that result in increased or decreased plant growth in a particular environmental condition or set of conditions. Some embodiments include one or more "agronomic trait(s)."

Correlated: As used herein with regard to traits or attributes, the term "correlated" may refer to a degree or proportion of variance that two traits share due to genetic causes. It may include, for example and without limitation, correlation associated with the proximity of two genes on the same chromosome, or correlation associated with genes that are expressed under the control of common genetic, molecular or environmental factors.

General combining abilities (GCA): As used herein, the term "general combining ability" may refer to a measure of the value of an inbred line as a parent of a hybrid.

Mixed-model analysis: As used herein, the term "mixed-model analysis" may refer to a system which contains experimental factors of both fixed and random-effects types, with appropriately different interpretations and analysis for the two types of factors.

Multivariate: As used herein, the term "multivariate" may refer to concurrent analysis of two or more variables of interest in an organism. These variables may be associated with a given trait, phenotype, gene, or allele. In some embodiments, these multiple variables may be correlated with each other.

Numerically representable phenotypic trait: As used herein, the term "numerically representable phenotypic trait" means a phenotypic trait that is susceptible to numerical description, i.e. a phenotypic trait that is quantitative or capable of being converted to a quantitative scale. Examples of such traits include yield, stalk strength, root strength, grain quality (oil quantity and quality, starch quantity and quality, amino acid and protein composition, vitamin composition, pigment, hardness, corn gluten meal and feed quality and quantity, disease resistance (including mycotoxin producing organisms, virus resistance, fungal resistance, bacterial resistance), stress resistance (including drought, chilling, freezing, high temperature, salt, oxidative), insect resistance, herbicide resistance, physiological plant characteristics (including seed drydown, standability, "stay green"), improved nutrient utilization, and male sterility. A preferred numerically representable phenotypic trait is yield, stalk strength, root strength, disease resistance, insect resistance, grain oil content, grain protein content, grain starch content, or grain moisture content, and a preferred plant species is Zea mays or Glycine max.

Phenotypic trait: As used herein, a phenotypic trait is a trait that is detectable and describable after visual inspection, measurement, or analysis by chemical, biochemical, or molecular techniques. A phenotypic trait is produced by the interactions of the genotype with the environment in which the plant develops. Units or factors that segregate when passing from parents to offspring exhibit the behavior expected of a single gene. The detectable appearance (phenotype) of an organism results from expression and interactions of genes with the environment. A phenotypic trait is a particular such detectable characteristic. Selection based on phenotype is only effective in altering traits in offspring if it changes the frequency of genes (the heritable factors) in the population under selection. Success in a traditional breeding program is thus a function of how closely the phenotype reflects the genotype. Some phenotypic traits are directly correlated with single gene segregation; that is, the genetic transmission from parent to offspring is reflected in phenotypic similarity. These are referred to as Mendelian, single locus, or single gene traits. Other traits do not show such direct links. Traits that fit in the latter category include those that are representable in numeric terms and show a continuous distribution when population values (X) are graphed. Such traits are referred to as "quantitative" or "continuous" traits. Those traits typically show a continuous distribution of values in a population, and are said to be under the control of quantitative trait locus (QTL).

Specific combining ability (SCA): As used herein, the term "specific combining ability" may be used to estimate the value of a parent line (e.g. an inbred parent) to generate a hybrid plant, where the estimation is based on an assessment of the hybrid plant itself.

Trait: As used herein, the term "trait" refers to a measurable characteristic of an individual. Certain traits may be useful in grouping or typing several individuals into a single cohort. The terms "trait" and "phenotype" are used interchangeably herein. Of particular interest in some embodiments of the invention are correlated traits, for example and without limitation, grain yield and moisture content.

Univariate: As used herein, the term "univariate" may refer to analysis of a single variable of interest in an organism. This variable may be associated with a given trait, phenotype, gene, or allele.

As used herein, the articles, "a," "an," and "the" include plural references unless the context clearly and unambiguously dictates otherwise.

IV. First Set of Embodiments

This disclosure provides a set of embodiments characterizing the multivariate mixed model approach for genetic evaluation of a plant.

Most phenotypic traits of commercial interest are under polygenic, rather than single locus, control. This means that expression of alleles at many loci contribute to the phenotype of interest. Polygenically controlled traits, therefore, are not solely determined by any particular locus. Consequently, selecting on the basis of phenotype is a superficial and inefficient strategy. Complex genetic phenomenon lurk underneath the phenotypic facade. A tortuous, rather than a direct path, links the phenotype and genotype. At best, previous methods for predicting progeny performance were based only on filial relationships, displayed diminished effectiveness when applied to contiguous generations, and were available only on a population basis, not for individual plants.

The basic concept of selection described above has been applied in specific breeding schemes. Success has been a function of how well inheritance of a trait fits the assumptions of the polygenic model, and of the factors discussed above. An important application of these polygenic models was in selective breeding programs aimed at channeling the values of the phenotype toward one end or the other of its distribution. Selection entails choosing a sample of potential parents, the sample being based on the value of the plants for the traits being selected.

Once inbred lines are created, the next step is to determine if the inbreds have any value. This is accomplished by techniques of measuring the combining ability of the new inbred plant, as well as the performance of the line itself. Combining ability refers to a lines contribution as a parent when crossed with other lines to form hybrids. Specific combining ability (SCA) refers to the ability of a line to cross to another specific inbred to form a hybrid. General combining ability (GCA) refers to the ability of a line to cross to a wide range of lines to form hybrids. The methodology of forming hybrids to evaluate an inbred lines contribution as a parent for the purpose of selecting superior lines is interchangeably known as experimental, top or test crossing.

General combining ability is the ability of an inbred to exhibit genetic compatibility with various sexual partners of varying pedigrees to provide an overall superior hybrid for each paired combination. The dominance is preferably across a wide variety of agronomically important traits. General combining ability is contrasted with "specific combining ability". Specific combining ability is present when the crossing of inbred A with inbred lines B through M provides a vigorous hybrid with inbred line B but agronomically poor vigor with inbred lines C through M.

General combining ability is important to the seed company as well as to the farming industry. An inbred with obvious positive agronomic traits and excellent general combining ability will most likely be utilized in more than one hybrid commercially. This provides the positive effects of this inbred's genetics to the farmers in more than one hybrid combination and most probably in more than one maturity.

Combining ability of a variety, as well as the performance of the variety per se, is a factor in the selection of improved maize inbreds. Combining ability refers to a variety's contribution as a parent when crossed with other varieties to form hybrids. The hybrids formed for the purpose of selecting superior varieties may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the varieties.

General combining ability provides an overall score for the inbred over a large number of test crosses. Specific combining ability provides information on hybrid combinations formed by the variety and a specific inbred parent. A variety that exhibits good general combining ability may be used in a large number of hybrid combinations.

Formation of a phenotypic database by quantitatively assessing one or more numerically representable phenotypic traits can be accomplished by making direct observations of such traits on progeny derived from artificial or natural self-pollination of a sample plant or by quantitatively assessing the combining ability of a sample plant.

Combining ability may be assessed by cross-breeding each sample of plant with a standard parental plant line having well-known characteristics. Testcrosses are assessed for a phenotypic trait of interest in a suitably designed field trial grown at one or more locations for one or more years. Such trials are conducted by measuring values of plants grown in specific "blocks" to control variance due to environmental factors such as soil type, drainage, soil water holding ability and the like. Trials are replicated to the extent necessary to control for plot error variance.

V. Second Set of Embodiments

A set of formulae and methods are provided for applying a univariate or multivariate mixed model approach to compute BLUPs, for use in genetic evaluation of an inbred plant.

The use of mixed linear models to compute BLUPs of random elements in the model may yield biased results if individuals in the population are not subjected to random sampling. For example, a distribution of a numerically representable phenotypic trait in a plant population that is obtained while selecting for a phenotype or trait of interest may not be sampled randomly with respect to the phenotypic trait, and thus a BLUP computed from this distribution may be biased. Methods to avoid biases in BLUPs computed from non-random distributions are known to mathematicians. See, e.g., Henderson (1975) Biometrics 31(2):423-47.

A univariate mixed linear model is assumed in some embodiments and can be represented as:

$$y = X\beta + Zu + e, \quad (3)$$

where y is an n×1 phenotypic observation vector, X is a known, n×p matrix, $\beta$ is an unknown, fixed vector, and Z is a known, n×q matrix. Thus, all fixed effects are modeled in the X$\beta$ term. u and e are nonobservable random vectors with null means and $$\mathrm{Var}\begin{bmatrix} u \\ e \end{bmatrix} = \begin{bmatrix} G & 0 \\ 0 & R \end{bmatrix}\sigma^2, \quad (4)$$

where $\sigma^2$ is a scalar, possibly unknown, and G and R are both nonsingular. u is a vector of polygene background effects, and e is a vector of residual effects. Eq. 3 may be expanded to include terms representing genetic marker effects (if marker information is available) and population effects. Yu et al. (2006) Nat. Genet. 38(2):203-8.

Now, given a sample vector, y, we wish to predict a linear function of $\beta$ and/or u.

If $\beta$ is unknown, as is usually the case, method invoking unbiasedness may be employed. By unbiased, we mean that $$E(k'+m'u) = k'\beta. \quad (5)$$

It has been shown that the best linear unbiased predictor (BLUP) of k'$\beta$−m'u is $$k'\hat{\beta} + m'GZ'V^{-1}(y - X\hat{\beta}), \quad (6)$$

where $\hat{\beta}$ is any solution to (7), the generalized least squares (GLS) equations, $$X'V^{-1}X\hat{\beta} = X'V^{-1}y. \quad (7)$$

See Henderson (1963) "Selection index and expected genetic advance." In *Statistical Genetics and Plant Breeding*, Hanson and Robinson (Eds.), National Academy of Sciences, National Research Council, WA, Publication 982, pp. 141-63.

A multivariate mixed model may be represented by:

$$\begin{bmatrix} y_1 \\ y_2 \\ y_3 \end{bmatrix} = \begin{bmatrix} X_1 & 0 & 0 \\ 0 & X_2 & 0 \\ 0 & 0 & X_3 \end{bmatrix}\begin{bmatrix} \beta_1 \\ \beta_2 \\ \beta_3 \end{bmatrix} + \begin{bmatrix} Z_1 & 0 & 0 \\ 0 & Z_2 & 0 \\ 0 & 0 & Z_3 \end{bmatrix}\begin{bmatrix} u_1 \\ u_2 \\ u_3 \end{bmatrix} + \begin{bmatrix} e_1 \\ e_2 \\ e_3 \end{bmatrix} \quad (8)$$

Wisser et al. (2011) Proc. Natl. Acad. Sci. U.S.A. 108(18):7339-44.

Eq. 8 may, like Eq. 3, be expanded to include terms representing genetic marker effects (if marker information is available) and population effects. Lund et al. (2003) Genetics 163:405-10.

The following examples are provided to illustrate certain particular features and/or embodiments. The examples should not be construed to limit the disclosure to the particular features or embodiments exemplified.

EXAMPLES

Example 1

Genetic Evaluation of Maize using Univariate and Multivariate Mixed Models

A multi-variate mixed model approach for genetic evaluation of maize was evaluated against the currently adopted uni-variate mixed model. Data for grain yield and moisture content was analyzed. General combining ability (GCA on inbred lines) and specific combining ability (SCA, reflecting the hybrid itself) values were determined. The two approaches were evaluated based on changes in accuracy of prediction of GCA, SCA, and hybrid performance. Overall, seven different data sets, derived from both experimental and existing commercial lines, were used for the comparison. The results were presented as predicted values, specifically as BLUPs, and accuracy of prediction.

All the analyses were conducted using ASREML 3.0 (Gilmour et al., 2009).

Uni-variate model. The uni-variate mixed model is the current statistical model used for the genetic evaluation of DAS maize germplasm. The model used in the present example is presented as:

$$y = X\beta + Ug_1 + Wg_2 + Zs + e \text{ (Backlund et al., 2006)}$$

where y is an (n×1) vector of phenotypic measurements on the individuals being evaluated following a specific distribution with mean Xβ and variance V; X and U, W and Z are design matrices of dimension (n×p), (n×r$_1$), (n×r$_2$) and (n×r$_3$), respectively (containing zeroes and ones for factors and coefficients in the case of regression type variables); β is a (p×1) vector of fixed effects; g$_1$ a (r$_1$×1) vector of random effects for the General Combining Ability (GCA) of the first parental lines (ex: female lines) to be evaluated; g$_2$ a (r$_2$×1) vector of random effects for the General Combining Ability (GCA) of the second parental lines (ex: male lines) to be evaluated; s a (r$_3$×1) vector of random effects for the Specific Combining Ability (SCA) of the hybrids to be evaluated; e a (n×1) vector of random errors (or a n×r matrix in case of repeated measurements) that also follow a specific distribution with a mean of 0 and a variance R.

The variance V would be calculated as:

$$V = UA_1U'\sigma^2_1 + WA_2W'\sigma^2_2 + ZDZ'\sigma^2_h + R$$

Multi-variate model. The multi-variate genetic evaluation mixed model can be represented using:

$$\begin{bmatrix} y_1 \\ y_2 \\ \vdots \\ y_i \end{bmatrix} = \begin{bmatrix} X_1 & 0 & 0 & 0 \\ 0 & X_2 & 0 & 0 \\ 0 & 0 & \ddots & 0 \\ 0 & 0 & 0 & X_i \end{bmatrix} \begin{bmatrix} \beta_1 \\ \beta_2 \\ \vdots \\ \beta_i \end{bmatrix} + \begin{bmatrix} U_1 & 0 & 0 & 0 \\ 0 & U_2 & 0 & 0 \\ 0 & 0 & \ddots & 0 \\ 0 & 0 & 0 & U_i \end{bmatrix} \begin{bmatrix} g_{11} \\ g_{21} \\ \vdots \\ g_{i1} \end{bmatrix} +$$

$$\begin{bmatrix} W_1 & 0 & 0 & 0 \\ 0 & W_2 & 0 & 0 \\ 0 & 0 & \ddots & 0 \\ 0 & 0 & 0 & W_i \end{bmatrix} \begin{bmatrix} g_{12} \\ g_{22} \\ \vdots \\ g_{i2} \end{bmatrix} + \begin{bmatrix} Z_1 & 0 & 0 & 0 \\ 0 & Z_2 & 0 & 0 \\ 0 & 0 & \ddots & 0 \\ 0 & 0 & 0 & Z_i \end{bmatrix} \begin{bmatrix} s_1 \\ s_2 \\ \vdots \\ s_i \end{bmatrix} + \begin{bmatrix} e_1 & 0 & 0 & 0 \\ 0 & e_2 & 0 & 0 \\ 0 & 0 & \ddots & 0 \\ 0 & 0 & 0 & e_i \end{bmatrix}$$

with "i" representing the trait of interest.

$$\begin{bmatrix} X_1 & 0 & 0 & 0 \\ 0 & X_2 & 0 & 0 \\ 0 & 0 & \ddots & 0 \\ 0 & 0 & 0 & X_i \end{bmatrix} \begin{bmatrix} \beta_1 \\ \beta_2 \\ \vdots \\ \beta_i \end{bmatrix}$$

represents the design matrices and fixed effects for each trait fitted in the model;

$$\begin{bmatrix} U_1 & 0 & 0 & 0 \\ 0 & U_2 & 0 & 0 \\ 0 & 0 & \ddots & 0 \\ 0 & 0 & 0 & U_i \end{bmatrix} \begin{bmatrix} g_{11} \\ g_{21} \\ \vdots \\ g_{i1} \end{bmatrix} +$$

$$\begin{bmatrix} W_1 & 0 & 0 & 0 \\ 0 & W_2 & 0 & 0 \\ 0 & 0 & \ddots & 0 \\ 0 & 0 & 0 & W_i \end{bmatrix} \begin{bmatrix} g_{12} \\ g_{22} \\ \vdots \\ g_{i2} \end{bmatrix} + \begin{bmatrix} Z_1 & 0 & 0 & 0 \\ 0 & Z_2 & 0 & 0 \\ 0 & 0 & \ddots & 0 \\ 0 & 0 & 0 & Z_i \end{bmatrix} \begin{bmatrix} s_1 \\ s_2 \\ \vdots \\ s_i \end{bmatrix}$$

represents the design matrices and random male and female GCA (g$_{i1}$ and g$_{i2}$ respectively) and SCA (s$_i$) for each trait "i" fitted in the model;

$$\begin{bmatrix} e_1 & 0 & 0 & 0 \\ 0 & e_2 & 0 & 0 \\ 0 & 0 & \ddots & 0 \\ 0 & 0 & 0 & e_i \end{bmatrix}$$

represents the random error term for each trait "i" fitted in the model;

The variance of the random effect:

$$\mathrm{Var}\begin{bmatrix} g_{11} \\ g_{21} \\ \vdots \\ g_{i1} \\ g_{12} \\ g_{22} \\ \vdots \\ g_{i2} \\ s_1 \\ s_2 \\ \vdots \\ s_i \end{bmatrix} = \begin{bmatrix} G_1 & 0 & 0 \\ 0 & G_2 & 0 \\ 0 & 0 & G_2 \end{bmatrix}$$

where G$_j$ represents the genetic covariance matrix for each genetic component j (j=GCA$_m$, GCA$_f$ or SCA).

The genetic correlation between the different genetic components (GCA$_m$, GCA$_f$ and SCA) is assumed to be zero. However correlations are usually assumed to exist between traits within each of these genetic components. Because the GCA is related to the additive genetic effect the genetic covariance matrix is of the form:

$$G_1 = \begin{bmatrix} A_1\sigma^2_1 & A_1\sigma_{11,21} & \ldots & A_1\sigma_{11,i1} \\ & A_1\sigma^2_{21} & \ldots & A_1\sigma_{21,i1} \\ & & \ddots & \\ & & & A_1\sigma^2_{i1} \end{bmatrix},$$

$$G_2 = \begin{bmatrix} A_2\sigma^2_{12} & A_2\sigma_{12,22} & \ldots & A_2\sigma_{12,i2} \\ & A_2\sigma^2_{22} & \ldots & A\sigma_{22,i2} \\ & & \ddots & \\ & & & A_2\sigma^2_{i2} \end{bmatrix},$$

$$G_3 = \begin{bmatrix} D\sigma^2_1 & D\sigma_{12} & \ldots & D\sigma_{1i} \\ & D\sigma^2_2 & \ldots & D\sigma_{2i} \\ & & \ddots & \\ & & & D\sigma^2_i \end{bmatrix}$$

where A$_1$ and A$_2$ the additive relationship matrices for the males and females respectively and D the dominance relationship matrix;

$\sigma^2_{kl}$ represents the genetic variance for trait k with l=male(1) or female(2), $\sigma_{kl,ml}$ represents the genetic correlation between traits k and m for l;

$\sigma^2_i$ represents the SCA genetic variance for trait i and $\sigma_{ij}$ represents the SCA genetic covariance between traits i and j.

The residual error matrix R can be presented as:

$$R = \begin{bmatrix} R_{11} & R_{12} & R_{13} & \cdots \\ R_{12} & R_{22} & \cdots & \cdots \\ R_{13} & \vdots & R_{33} & \cdots \\ \cdots & \cdots & \cdots & \end{bmatrix}$$

where $R_{ii}$ represents the residual error variance structure for trait i and $R_{ij}$ represents the residual error covariance structure for traits i and j although most of the time this covariance is assumed to be zero.

$R_{ii}$ can take on several structures (ex: Identity, Auto-Regression, Unstructured, etc. . . . ) and can be different for each trait.

The model used for the analysis of yield and moisture included a type effect to account for entries being used as check (1) or as hybrids (2), treated as fixed, which allows for estimating two separate overall population means, one for the checks and another for the hybrids. In addition, female parent, male parent, hybrid, check and BlockID are incorporated into the model and treated as random. The female parent and male parent were assumed to follow a random normal distribution with a mean of zero and a co-variance matrix $G_1$ and $G_2$ respectively while the hybrid effect (SCA) was assumed to follow a random normal distribution with a mean of zero and a co-variance matrix $G_3$. The random effect of check and BlockID were each assumed to be normally, identically and independently distributed (NIID).

Methods for comparing the results. For genetic evaluation, the results from each modeling approach were compared by looking at changes affecting the accuracy of prediction of the genetic values. Accuracy measures the correlation between the predicted genetic value (BLUP value) and the "true" genetic value. This measure is based on the prediction error variance (PEV) (i.e. the variance of genetic value) of the line in question, the genetic variance component estimate ($\sigma^2$) of the population from which this line is coming and the diagonal element of the relationship matrix used in performing the genetic evaluation of the line in question. The accuracy of prediction was calculated using $$R = \sqrt{1 - \frac{PEV}{[(aii)\sigma^2]}}$$

A percent change was calculated to assess the direction of the change between the accuracies of prediction of the uni-variate model and the multi-variate model. Also, a Spearman rank correlation (e.g. Wackerly et al., 2002) was used to detect the correlation between the ranking of the lines, based on their GCA and SCA values, from the two approaches.

Results. For grain yield and moisture content, increases in accuracy of prediction for GCA from using the multi-variate approach averaged between 1% and 45% depending on the data set; for SCA, increases in accuracy from using the multi-variate approach averaged between 0.3% and 7% depending on the data set. For GCA, increases in accuracy from using the multivariate approach averaged between 1% and 45% depending on the data set. For SCA, increases in accuracy from using the multivariate approach averaged between 0.3% and 7% depending on the data set. Spearman rank correlations were generally high with an overall average of 0.93 indicating small changes in ranking between the two modeling approaches.

The genetic evaluation of maize for grain yield and moisture content could therefore be improved by the evaluation of the germplasms for both traits simultaneously, rather than individually.

What may be claimed is:

1. A multivariate mixed model method for genetic evaluation of an inbred maize plant and a hybrid maize plant, the multivariate mixed model method comprising the steps of:
   a) quantitatively assessing the distribution of two or more traits of interest in a population of inbred maize plants, wherein the traits of interest comprise a plurality of correlated attributes comprising grain yield and moisture content;
   b) constructing a relationship matrix for each inbred maize plant parent for the two or more traits of interest;
   c) applying the relationship matrix in a multivariate mixed model analysis for the population of inbred maize plants;
   d) generating field trial data for hybrid progeny of the population of inbred maize plants, wherein the field trial data for the hybrid progeny are analyzed with the multivariate mixed model analysis; and
   e) obtaining a predicted genetic value for said inbred maize plant, wherein the predicted genetic value includes a general combining ability (GCA) value, a specific combining ability (SCA) value, or both the GCA value and the SCA value for the population of inbred maize plants.

2. The multivariate mixed model method according to claim 1, wherein the population of inbred maize plants is separated into male and female lines.

3. The multivariate mixed model method according to claim 1, wherein the plurality of correlated attributes consists of grain yield and moisture content.

4. The multivariate mixed model method according to claim 1, the method further comprising determining the general combining ability for said inbred maize plant.

5. The multivariate mixed model method according to claim 1, the method further comprising constructing a dominance relationship matrix to determine the specific combining ability for said inbred maize plant.

6. The multivariate mixed model method according to claim 1, the method further comprising calculating a BLUP using the model.

7. The multivariate mixed model method according to claim 1, the method further comprising calculating the accuracy of prediction for the predicted genetic value.

8. The multivariate mixed model method according to claim 1, the method further comprising the step of selecting an inbred plant using the predicted genetic value obtained.

9. A multivariate mixed model method for selecting an inbred maize plant and a hybrid maize plant, the multivariate mixed model method comprising:
   a) quantitatively assessing the distribution of two or more traits of interest in a population of inbred maize plants, wherein the traits of interest comprise a plurality of correlated attributes comprising grain yield and moisture content;
   b) constructing a relationship matrix for each inbred maize plant parent for the two or more traits of interest;
   c) applying the relationship matrix in a multivariate mixed model analysis for the population of inbred maize plants;

d) generating field trial data for hybrid progeny of the population of inbred maize plants, wherein the field trial data for the hybrid progeny are analyzed with the multivariate mixed model analysis; and e) selecting one or more inbred maize plants based on a predicted genetic value, wherein the predicted genetic value includes a general combining ability (GCA) value, a specific combining ability (SCA) value, or both the GCA value and the SCA value for the population of inbred maize plants.

10. The multivariate mixed model method according to claim 9, wherein the population of inbred maize plants is separated into male and female lines.

11. The multivariate mixed model method according to claim 9, wherein the plurality of correlated attributes consists of grain yield and moisture content.

12. The multivariate mixed model method according to claim 9, the method further comprising determining the general combining ability for said inbred maize plant.

13. The multivariate mixed model method according to claim 9, the method further comprising constructing a dominance relationship matrix to determine the specific combining ability for said inbred maize plant.

14. The multivariate mixed model method according to claim 9, the method further comprising calculating a BLUP using the model.

15. The multivariate mixed model method according to claim 9, the method further comprising calculating the accuracy of prediction for the predicted genetic value.

16. The multivariate mixed model method according to claim 9, the method further comprising selecting a hybrid progeny plant based on predicted genetic values obtained from two parent inbred maize plants.

* * * * *